United States Patent [19]

Starner et al.

[11] 4,332,736

[45] Jun. 1, 1982

[54] PRODUCTION OF 1-HYDROXYALKYLIDENE-1, 1-DIPHOSPHONIC ACID ESTERS

[75] Inventors: William E. Starner, Freeland; Walter F. Yext, Mahanoy City, both of Pa.

[73] Assignee: Air Products and Chemicals, Inc., Allentown, Pa.

[21] Appl. No.: 190,009

[22] Filed: Sep. 22, 1980

[51] Int. Cl.³ .............................................. C07F 9/38
[52] U.S. Cl. .................................. 260/403; 560/266; 260/502.4 A
[58] Field of Search ................. 260/502.4 A, 410.9 R, 260/403; 560/266

[56] References Cited

U.S. PATENT DOCUMENTS 3,959,360  5/1976  Vazopolos .................... 260/502.4 P

FOREIGN PATENT DOCUMENTS 1102525  2/1968  United Kingdom ......... 260/502.4 P

Primary Examiner—Joseph E. Evans
Attorney, Agent, or Firm—Russell L. Brewer; E. Eugene Innis; James C. Simmons

[57] ABSTRACT

Acylated 1-hydroxyalkylidene-1, 1-diphosphonic acid (HADPA) can be produced almost instantaneously with less than 5% (by weight) phosphorus acid by-product by introducing $PX_3$ (where X is a halide) into a reactor containing R—COOH at or above a specified temperature. The acylated HADPA can then be hydrolyzed and substantially pure HADPA obtained by vacuum distillation. Of particular importance is the addition of $PCl_3$ to acetic acid at a temperature of between 105° C. and 120° C. to produce acetylated 1-hydroxyethylidene-1, 1-diphosphonic acid (HEDPA).

8 Claims, 1 Drawing Figure

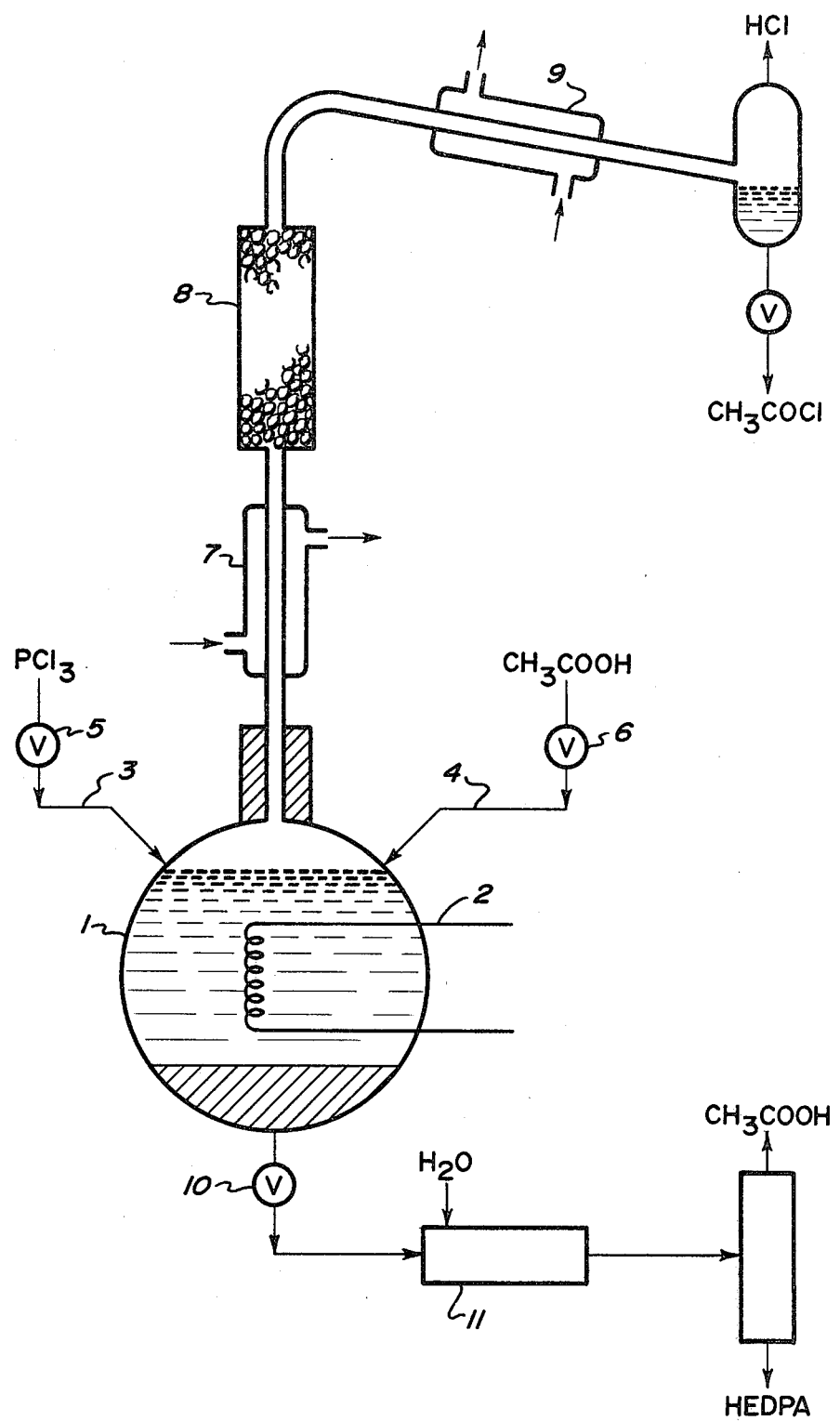

PRODUCTION OF 1-HYDROXYALKYLIDENE-1, 1-DIPHOSPHONIC ACID ESTERS

TECHNICAL FIELD

This invention relates to a method for producing 1-hydroxyalkylidene-1, 1-diphosphonic acid, hereinafter referred to as HADPA, and more particularly but not exclusively is concerned with a method of producing 1-hydroxyethylidene-1, 1-diphosphonic acid, hereinafter referred to as HEDPA.

HADPA is used inter alia as a descaling agent and in secondary oil recovery.

PRIOR ART

A number of processes have been described which involve reacting phosphorus trichloride with acetic acid as the first step towards producing HEDPA. Typically, the phosphorus trichloride is mixed with the acetic acid at room temperature and reacts within a few minutes to form phosphorus acid and acetyl chloride. The temperature is then gradually raised to between 60° C. and 110° C. during which time the system is kept under total reflux and acetylated HEDPA is formed. As the concentration of acetylated HEDPA increases, it forms a separate phase which contains phosphorus acid. However, phosphorus acid and acetylated HEDPA cannot be readily be separated and the reaction has to be continued for several hours until the concentrations of phosphorus acid in the phase reaches an acceptable level, i.e. below 5% [by weight]. The acetylated HEDPA is then hydrolized and substantially pure HADPA recovered.

As noted in the prior art particularly U.S. Pat. No. 3,366,676 the reaction of PCl₃ and acetic acid was difficult to control at atmosphere pressure because of the high volatility of acetyl chloride formed on initial reaction. Long reaction times were required; additionally the final and intermediate reaction products often precipitated in a semisolid heterogeneous mass.

Example III of U.S. Pat. No. 3,366,376 discloses adding PCl₃ to a solution of acetic acid and tributylamine. The mixture was heated to 280° F. (136° C. ) in a closed reactor over a period of 9 minutes after which only traces of unreacted phosphite ion were detected. However, the presence of the amine complicates recovery of HEDPA.

SUMMARY OF THE INVENTION

Contrary to any predictable behavior, we have discovered that if phosphorous trichloride is added directly to acetic acid at or above 100° C., then acetylated HEDPA is produced almost instantaneously. At 100° C. a small [but acceptable] amount of phosphorus acid by-product is produced. If the acetic acid is maintained at a higher temperature, for example, 115° C. then an even smaller amount of phosphorus acid by-product is formed. In addition the process will operate at atmospheric pressure and can easily be adapted to continuous operation.

We have observed similar behavior using octanoic acid in place of acetic acid although in this case we recommend that the octanoic acid should be maintained at or above 150° C.

According to the present invention there is provided a method of producing acylated HADPA comprising introducing PX₃, where X is a halide, into a reactor containing R—COOH where R is an alkyl group containing from 1 to 18, preferably 1 to 8, and more preferably 1 to 4, carbon atoms to produce acylated HADPA, an organic halide and HX characterized in that said R—COOH is at or above a temperature T such that the weight of phosphorus acid by-product detectable by iodometric titration at any time during said reaction is less than 5% of the total weight of the acylated HADPA and phosphorus acid formed.

The lowest value of T for each carboxylic acid can be determined experimentally. However, as a rule of thumb, where R contains between 1 and 4 carbon atoms the minimum value of T will be between 100° C. and 130° C. and where R contains between 5 and 18 carbon atoms the minimum value of T will be between 130° C. and 180° C.

The highest temperature which can be used is just below the temperature at which the acylated HADPA decomposes. However, it is generally desirable to use a lower temperature since discoloration of the acylated HADPA frequently occurs well below its decomposition temperature.

The organic halide and HX formed with the acylated HADPA are preferably allowed to distill from the reactor as they are formed and the acylated HADPA is preferably allowed to accumulate in the reactor until it forms a separate and distinct phase from the carboxylic acid. This phase can then be readily withdrawn and the acylated HADPA hydrolized. The resulting mixture is then distilled to produce substantially pure HADPA. This procedure is particularly suited to the continuous production of HADPA.

In one particularly preferred embodiment, X is Cl and R is CH₃. When this is the case and the continuous production of HEDPA is contemplated, once the reaction is running smoothly, both phosphorus trichloride and acetic acid are introduced into the reactor preferably in the ratio from about 1:3 to about 1:5 [by moles]. The temperature T should be maintained at above 105° C. and preferably between 105° C. and 120° C. since below 100° C. substantial amounts of phosphorus acid are formed whereas above 120° C. the acetylated HEDPA tends to discolor. In this connection the reactor could theoretically be maintained at up to 179° C. above which temperature the acetylated HEDPA would decompose. Similar considerations regarding temperature would apply to the batch production of HEDPA.

Hydrolysis of the acetylated HADPA may be carried out between the freezing point and decomposition temperature of the acylated HADPA. In the case of acetylated HEDPA this would be between 10° C. and a 180° C. at NTP, although temperatures between 90° C. and 120° C. are recommended since at these temperatures the acetylated HEDPA is relatively simple to handle and hydrolzes instantly.

After hydrolysis the HADPA is preferably separated from other organics by vacuum distillation. Again, in the case of HEDPA temperatures between 0° C. and 180° C. could be used although it is recommended that temperatures between 80° and 120° C. be used at pressures from 10 to 50 mm mercury.

For a better understanding of the invention and to show how the same may be carried into effect reference will now be made to the following Examples and the accompanying drawing which shows an apparatus in which the present invention may be carried out.

EXAMPLE 1

Referring to the drawing 180 g [3 M] of acetic acid was charged to a 500 ml glass reactor 1. The acetic acid was then heated to 115° C. by circulating oil at 155° C. through a heating coil 2 in the reactor 1.

Phosphorus trichloride and acetic acid were then continuous admitted to the reactor 1 through lines 3 and 4 by opening valves 5 and 6 respectively. The phosphorus trichloride was admitted to the reactor over an 8 hour period at the rate of 68 g [0.5 M]/hr. and the acetic acid was admitted to the reactor 1 to maintain the total volume of liquid in the reactor constant.

It is believed that the phosphorus trichloride reacted with the acetic acid in accordance with the reaction:

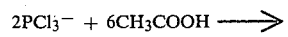

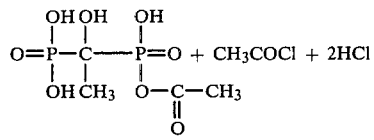

which appeared to proceed instantaneously.

The temperature was maintained between 105° C. and 120° C. throughout the entire process and hence the acetyl chloride and hydrochloric acid distilled off as it was produced and after passing through condenser 7 and column 8 packed with ¼" ceramic saddles was passed through condenser 9 where the acetyl chloride condensed at the rate of 62.6 g/hr. The majority of acetic acid entrained with the acetyl chloride and hydrochloric acid condensed in condenser 7 and the balance in column 8.

After 1 hour, during which time sufficient HEDPA was formed to produce a usable separate and distinct phase, valve 10 was opened and acetylated HEDPA continuously removed from the bottom of the reactor 1 at the rate of 81 g/hr.

The acetylated HEDPA was then mixed with water in the ratio 1 part acetylated HEDPA to 0.13 parts water [by weight] in an in-line mixer 11 where the following reaction occurred:

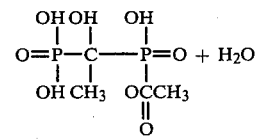

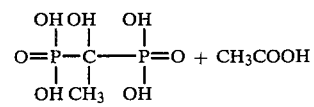

The acetic acid and excess water was then removed from the HEDPA by vacuum distillation at 115° C. and 20 millimeters mercury pressure and product HEDPA collected as liquid at the rate of 51.1 g/hr.

The yield for acetylchloride, based on the phosphorus trichloride charge, was approximately 80.6% and the yield for the product HEDPA, based on the phosphorus trichloride charge, was approximately 97.5%.

It was noted that the phase containing acetylated HEDPA contained 2.65% phosphorus acid [by weight].

The amount of acetic acid introduced into the glass reactor 1 averaged 90 g (1.5 M/hr) after valve 10 was opened.

At no time during the entire reaction (either before or after valve 10 was opened) was more than 5% by weight of phosphorus acid detected by iodometric analysis in the total phosphorus acid and HEDPA formed.

It will be noted that the acetyl chloride was not recycled and that the reaction proceeded at atmospheric pressure. Furthermore no amines are present to inhibit recovery of the HEDPA.

EXAMPLE 2

In order to show the unexpected nature of the present invention 180 gms [3 moles] acetic acid were mixed with a 137 gms [1 mole] PCl₃ at 30° C. The mixture was then agitated for five minutes and heated to 115° C. over a period of 10 minutes. Acetyl chloride started boiling off at 38° C. It was found that after the mixture had been maintained at 115° C. for 0.5 hours the phase containing HEDPA also contained 20.8% (by weight) phosphorus acid. After a further 23.5 hours at 115° C., the amount of phosphorus acid present had not dropped at all.

EXAMPLE 3

144 gms [1M] of octanoic acid was charged to a 500 ml glass reactor. The octanoic acid was then heated to 150° C. by circulating oil through a heating coil in the reactor. The pressure was then reduced to 100 mm Hg.

Phosphorus trichloride and octanoic acid were then continuously admitted to the reactor. The phosphorus trichloride was sparged directly into the octanoic acid via a sintered glass sparger at the rate of 68.5 gm (0.5 M)/hr. and the octanoic acid was admitted to the reactor to maintain the total volume of liquid in the reactor constant. This averaged 216 g (1.5 M)/hr. of octanoic acid.

Acryl 1-hydroxyoctane-1, 1-diphosphoric acid (HODPA) appeared to be formed instantaneously and formed a separate phase which was removed from the reactor at the rate of 100 gm/hr. The octanoyl chloride and hydrochloric acid were distilled off as they were formed.

The phase containing the HODPA contained 1.9% phosphorus acid.

A yield of 98% HODPA was obtained based on the PCl₃ and a yield of 81.2% octanoyl chloride was obtained based on PCl₃.

In each of the above examples the Iodometric titrations were carried out withdrawing 1 ml samples:
1. From the reactor before the two phases formed; and
2. From the bottom layer after the two phases formed.

Each sample was first neutralized with sodium carbonate. 50 ml of 0.1 N aqueous iodine was then added and the solution was allowed to rest for 20 minutes. The solution was then titrated with sodium thiosulphate and the amount of phosphorus acid present calculated from the result.

What is claimed is:
1. In a process for producing an acylated 1-hydroxy alkylidene-1,1-diphosphonic acid (HADPA) by reacting $PX_3$, where X is a halogen atom and RCOOH where R is an alkyl group containing from 1–18 carbon atoms to produce said acylated HAPDA, the improvement which comprises:

introducing said $PX_3$ to a reactor containing RCOOH;

maintaining RCOOH during said introduction of $PX_3$ at a temperature T such that the resulting reaction between RCOOH and $PX_3$ results in producing a product mixture comprising acylated HAPDA and by-product phosphorous acid, said temperature being at or greater than 100° C. where R is an integer from 1-4 and at or greater than 130° C. where R is an integer from 5-18 carbon atoms whereby the by-product phosphorous acid detectable by iodometric titration at any time in the product mixture is less than 5% of the total weight of the acylated HADPA and phosphorous acid formed.

2. A process according to claim 1 wherein the temperature T is above the boiling temperature of the organic halide and HX and said organic halide and HX are distilled from the reactor as they are formed.

3. A method according to claim 2, characterized in that the acylated HADPA is allowed to accumulate in said reactor until it forms a separate and distinct layer from said carboxylic acid.

4. A method according to claim 1, characterized in that X is Cl.

5. A method according to claim 4, characterized in that R is $CH_3$.

6. A method according to claim 5, characterized in that the $PCl_3$ and $CH_3COOH$ are admitted to the reactor in the ratio from about 1:3 to about 1:5 [by moles].

7. A method according to claim 5 or 6, characterized in that the temperature of the acetic acid is maintained between 105° C. and 120° C.

8. A method according to claim 4, characterized in that R-COOH is octanoic acid and T is equal to or greater than 150° C.

* * * * *